United States Patent
Kazmi et al.

(10) Patent No.: US 11,590,071 B2
(45) Date of Patent: Feb. 28, 2023

(54) INJECTABLE DRUG DELIVERY IMPLANT COMPOSITION AND METHOD OF USE THEREOF

(71) Applicant: King Abdulaziz University, Jeddah (SA)

(72) Inventors: Imran Kazmi, Jeddah (SA); Hemant Yadav, Jeddah (SA); Fahad Fahad A. Al-Abbasi, Jeddah (SA); Muhammad Shahid Nadeem, Jeddah (SA); Hisham Altayeb, Jeddah (SA); Muhammad Afzal, Jeddah (SA); Gaurav Gupta, Jeddah (SA); Abhay Raizaday, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 16 days.

(21) Appl. No.: 17/367,967

(22) Filed: Jul. 6, 2021

(65) Prior Publication Data
US 2023/0017509 A1   Jan. 19, 2023

(51) Int. Cl.
| | |
|---|---|
| A61K 31/225 | (2006.01) |
| A61K 47/36 | (2006.01) |
| A61K 47/20 | (2006.01) |
| A61P 25/00 | (2006.01) |
| A61K 9/00 | (2006.01) |
| A61P 21/00 | (2006.01) |

(52) U.S. Cl.
CPC .......... *A61K 9/0019* (2013.01); *A61K 31/225* (2013.01); *A61K 47/20* (2013.01); *A61K 47/36* (2013.01); *A61P 21/00* (2018.01)

(58) Field of Classification Search
CPC .... A61K 31/225; A61K 9/0019; A61K 47/36; A61K 47/38; A61K 47/20; A61P 21/00; A61P 25/00
See application file for complete search history.

(56) References Cited

U.S. PATENT DOCUMENTS

| | | |
|---|---|---|
| 2017/0231917 A1 | 8/2017 | Wooster |
| 2019/0070143 A1* | 3/2019 | Boulas ................ A61K 47/10 |
| 2020/0155475 A1 | 5/2020 | Lakhani |

OTHER PUBLICATIONS

Du et al. Macromol. Biosci. 2012, 12, 952-961.*
Palumbo et al. Carbohydrate polymers 2020, 229, 115430, p. 1-19.*
Krauland et al. Journal of Pharmaceutical Sciences 2003, 92 (6), 1234-1241.*

* cited by examiner

Primary Examiner — Irina Neagu
(74) Attorney, Agent, or Firm — WCF IP

(57) ABSTRACT

Provided are an injectable and implantable drug delivery composition and a method for using such composition to release active ingredients and/or pharmaceutical agents to a site of action. The composition includes a gellan-gum cross-linked with L-cysteine and at least one pharmaceutical active agent in a biocompatible solvent.

10 Claims, 13 Drawing Sheets

INJECTABLE DRUG DELIVERY IMPLANT COMPOSITION AND METHOD OF USE THEREOF

FIELD OF THE INVENTION

The disclosure provides an injectable and implantable composition and a method of using such composition for releasing an active ingredient within the site of action after a pre-determined time following the injection. In particular, the invention provides an injectable and implantable composition that includes a biologically active agent in a L-cysteine crosslinked native polymer of gellan gum. The injectable gellan gum polymer containing drug delivery implants are biodegradable and suitable for the release of pharmaceutical agents over time when the composition is parenterally injected.

BACKGROUND

Treatment for chronic diseases often involve a long-term pharmaceutical therapy. For some conditions, two or more injections per day may be required and thus may lead to poor patient compliance. Biodegradable polymers are well known for their use in biomedical applications such as sutures, surgical clips, staples, implants and other forms of drug delivery systems. However, most of the currently known biodegradable polymers are solid materials that are used to form solid articles such as implants or surgically inserted microcapsules. In addition, prolonged drug delivery by means of injections, inhalation, transdermal, or swallowing pills or capsules generally results in varying drug concentrations in the system and between each dosing period. The local inflammatory reaction triggered by repeated medication injections may also increase poor patient compliance, resulting in an incomplete drug therapy. For this reason, the implantable and injectable drug delivery system has attracted great interest for its potential uses in overcoming the limitations including inconsistency in the drug delivery to the site of action (Hatefi and Amsden, 2002). For example, runny formulations which are also known as liquid implants to create a semi-solid depot following subcutaneous injection are considered to be an attractive parenteral delivery system for many reasons. In contrast to using solid implants, which require an anesthesiology local and a small procedure, the drug delivery procedures of runny formulation are less invasive or traumatic. Such runny, liquid composition can be designed for longer durations, usually from one to multiple months, and for local or systemic drug distribution. (Packhaeuser et al., 2004).

The use of water-dissolving polymers, which can form a gel after use at the delivery site, are also known in the art. In comparison to much more powerful gels, this gelling polymers of so called in-situ are highly lucrative because they can be simply applied on drug absorption site in the form of fluid. When injected into the body, the water-dissolving polymers enlarge to create a solid gel that can extend the active substance's retention time. These types of delivery system offer a number of advantages including the ease of manufacture of the polymer solution, the incorporation of the drug into the polymer solution just prior to administration leading to increased drug and polymer stability as well as no loss of drug during the manufacturing process, and the ability to terminally sterilize the polymer solution as well as the drug. However, the main disadvantage of the natural water-soluble polymer is that they possess poor gelation properties, and they also trigger immunogenic reaction at the site of application. In addition, the water-soluble polymer delivery system may not be suitable for some since the injection is primarily limited to a subcutaneous region where the injected material may form quite distinct and noticeable bumps. Further, some of the solvents commonly used in these delivery systems may cause unfavorable side effects due to their potential toxicity in the body.

Thus, there is a need for a method and composition for providing liquid polymeric implants with low viscosity sufficient for ease of injection yet improved gelation property. In addition, there is a need in the art for implantable and injectable polymeric implant compositions that are biodegradable, non-toxic and capable of providing easy administration into the body using standard syringes and needles.

SUMMARY OF THE INVENTION

An object of the invention is to provide an injectable and implantable drug delivery composition and a method of using such system for treating a subject in need thereof. The system is designed to release an active ingredient within the site of action following the injection. One of the advantageous features of the present invention includes the incorporation of polymeric materials (e.g., gellan-gum) for containing a drug and by using L-cysteine to improve the gelation property as well as immunogenic property of the in situ implantable drug delivery system.

One aspect of the disclosure provides an injectable drug delivery implant composition which comprises a biodegradable water-soluble polymer of gellan gum which is crosslinked with L-cysteine; a biocompatible solvent; and a therapeutically effective amount of a biologically active agent to be parenterally injected into the body of a subject in need thereof. The composition is in a liquid form before the injection and becomes a gel-like implant after the injection in situ. In some embodiments, the gellan gum crosslinked with L-cysteine has a concentration of 0.5-3% by weight based on the total weight of the composition. In some embodiments, the biocompatible solvent is 5-25% v/v of water or DMSO. In preferred embodiments, the gellan gum crosslinked with L-cysteine to the biologically active agent is at a 0.5:1 to 3:1% w/w ratio.

Another aspect of the disclosure provides an implantable and injectable drug delivery composition which provides a controlled release of a biologically active agent through an in situ forming implant (ISFI). In some embodiments, dimethyl fumarate (DMF) is an exemplary biologically active agent. In such cases, the implant composition comprises a biodegradable water-soluble polymer of gellan gum crosslinked with L-cysteine; a biocompatible solvent; and a therapeutically effective amount of a biologically active agent to be parenterally injected into a body of a subject in need thereof, wherein the biologically active agent is dimethyl fumarate (DMF) or pharmaceutically acceptable salts thereof, wherein the composition is in a liquid form before the injection, and wherein the composition undergoes gelation to form a gel-like implant after the injection. In some embodiments, the gellan gum crosslinked with L-cysteine has a concentration of 0.5-3% by weight based on the total weight of the composition. In some embodiments, the biocompatible solvent is 5-25% v/v of water or DMSO. In preferred embodiments, the gellan gum crosslinked with L-cysteine to the biologically active agent is at a 0.5:1 to 3:1% w/w ratio.

Yet another preferred embodiment of the disclosure provides a method of treating a subject with multiple sclerosis (MS). The method comprises a step of parenterally injecting under the skin of the subject a composition of gellan gum crosslinked with L-cysteine and a medication suitable for MS distributed therein, wherein the medication suitable for MS is releasable from the gellan gum crosslinked with L-cysteine over time, and wherein the gellan gum crosslinked with L-cysteine is biodegradable. In preferred embodiments, the medication suitable for MS is DMF or pharmaceutically acceptable salts thereof. In some embodiments, the gellan gum crosslinked with L-cysteine has a concentration of 0.5-3% by weight based on the total weight of the composition. In some embodiments, the biocompatible solvent is 5-25% v/v of water or DMSO. In preferred embodiments, the gellan gum crosslinked with L-cysteine to the biologically active agent is at a 0.5:1 to 3:1% w/w ratio.

Additional features and advantages of the present invention will be set forth in the description of disclosure that follows, and in part will be apparent from the description of may be learned by practice of the disclosure. The disclosure will be realized and attained by the compositions and methods particularly pointed out in the written description and claims hereof.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

Figure 1:
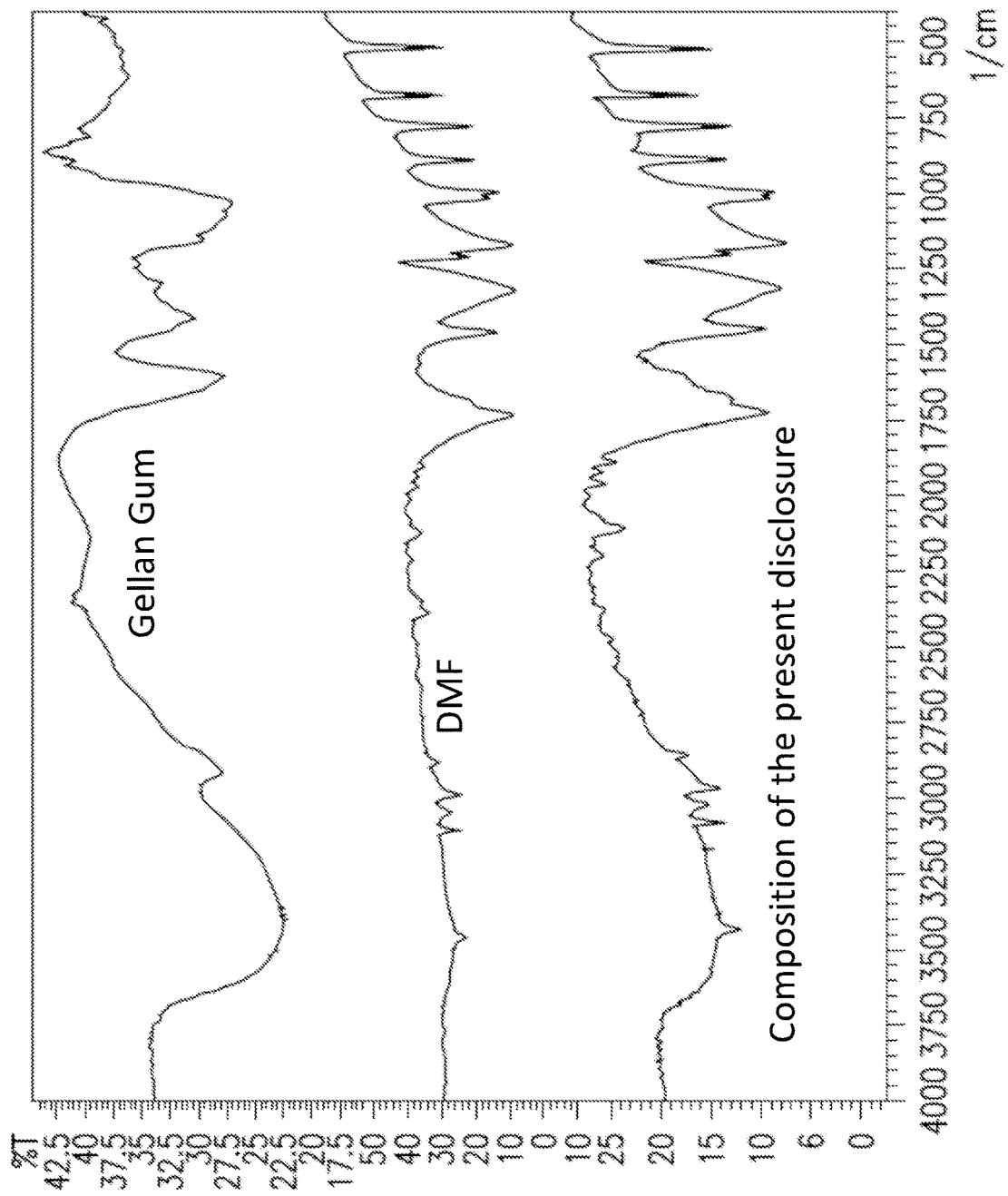
FIG. 1 shows FTIR spectra of the Gellan Gum, DMF and the composition of the present disclosure.

The preferred embodiments of the present disclosure are directed toward an injectable and implantable drug delivery composition and a method of using the composition for releasing biologically active agents when administered in the body of a subject in need thereof. The composition is particularly formulated with an aid of a natural gellan gum polymer to provide superior flexibility and viscosity. The gellan gum polymer is further crosslinked with L-cysteine for a stable solution to gel-like transition in situ on the basis of oxidation.

One aspect of the disclosure provides an injectable drug delivery implant composition which comprises a biodegradable water-soluble polymer of gellan gum in a L-cysteine-crosslinked form; a biocompatible solvent; and a therapeutically effective amount of a biologically active agent to be parenterally injected into the body of a subject in need thereof. The composition is in a liquid form before the injection and becomes a gel-like implant after the injection in situ. As used herein, the term "liquid" refers to the ability of the composition and/or the liquid polymer material or implants to undergo continuous deformation under a shearing stress. The liquid compositions of the present invention possess a viscosity, density and flowability to allow delivery of the composition through small gauge needles (e.g., 18-26 gauge) with low to moderate injection force using standard syringes. The liquid composition has a definite volume but is an amorphous liquid mass with no definite shape. As used herein, the term "gel" or "gel-like" refers to a gelatinous semisolid composition with a resilient consistency and yet a composition that exhibits no flow when in the steady-state. Unlike a liquid composition, a gel-like composition may have a definite shape depending on varying hardness of the gel structure. As used herein, the term "gelation" refers to a condition where the system (i.e., liquid composition) loses fluidity and gains sufficient viscosity to form a gel. For example, branched polymers can form links between the chains and progressively build a larger polymer linkage resulting in the formation of a single macroscopic molecule. The gelation may be promoted by gelling agents and/or by other physical linking or chemical crosslinking.

In some embodiments, the gellan gum crosslinked with L-cysteine has a concentration of 0.5-3% by weight based on the total weight of the composition. Gellan gum is a water-soluble anionic polysaccharide produced by bacteria and used herein as an exemplary natural water-soluble polymer. As an approved polymer for food use, gellan gum in the drug delivery composition of the present disclosure provides biodegradability, safety and viscosity sufficient to be used as a thickener, emulsifier and stabilizer. The gellan gum is crosslinked with L-cysteine, in which the gellan gum may be in a deacetylated or acetylated form. Further, the polymer gellan gum may be linear, branched, grafted and/or star-shaped. Due to the lack of having definite structures, liquid polymers with their amorphous states do not typically provide an extended release of the contained biologically active agent. In addition, commonly added organic solvents to a typical liquid drug delivery system composition do not provide an extended release of a drug. The present injectable drug delivery implant composition uses water or DMSO as a biocompatible solvent as well as providing gelation effect so that the injected composition in a liquid form becomes a gel-like implant that does not completely solidify into a solid form in the body. Thus, the gel composition provides comparable initial burst like those observed with liquid composition in addition to extended release of biologically active agents similar to those observed with solid implant. In some embodiments, the biocompatible solvent is 5-25% v/v of water. In other embodiments, the biocompatible solvent is 5-25% v/v of DMSO. In preferred embodiments, the gellan gum crosslinked with L-cysteine to the biologically active agent is at a 0.5:1 to 3:1 ratio. In some embodiments, all components of the drug delivery implant composition are natural materials and biodegradable. Further, the composition is readily injectable and sterile filterable. Because the injected composition is made of natural materials and in a gel-like formation, the composition releases the containing bioactive material without tissue irritation or noticeable bumps associated with solid implants.

Another aspect of the disclosure provides an implantable and injectable drug delivery composition, of which provides a controlled subcutaneous release of a biologically active agent through an in situ forming implant. In some embodiments, one active agent is in the composition for each injection. In other embodiments, a combination of active agents is in the composition. Some exemplary biologically active agents include, but are not limited to, one or more antihistamines, potassium channel blockers, antidiabetic agents, pain-relief agents, vasodilators, diuretics, antiaging agents, antibacterial agents, antifungal agents, GERD medications, anti-inflammatory agents, chemotherapeutic agents, and central nervous system regulators. Exemplary anti-Parkinson's medications include, but are not limited to, levodopa, carbidopa, ropinirole, pramipexole, rotigotine, apomorphine, selegine, hydrochloride and benztropine. Exemplary Multiple Sclerosis (MS) medications include, but are not limited to, teriflunomide, dalfampridine, dimethyl fumarate, natalizumab, fingolimod and glatiramer acetate. Exemplary GERD medications include, but are not limited to, esomeprazole, omeprazole and pantoprazole.

In some embodiments, dimethyl fumarate (DMF) is an exemplary biologically active agent. In such cases, the implant composition comprises a biodegradable water-soluble polymer of gellan gum crosslinked with L-cysteine, a biocompatible solvent, and a therapeutically effective amount of a biologically active agent to be parenterally injected into a body of a subject in need thereof, wherein the biologically active agent is dimethyl fumarate (DMF) or pharmaceutically acceptable salts thereof, wherein the composition is in a liquid form before the injection, and wherein the composition become a gel-like form after the injection as the composition system that undergoes a gelation.

The biocompatible solvents that can be used according to the invention are non-toxic and can be either hydrophilic or slightly lipophilic depending upon the desired release profile as well as the solubility of the polymer and biologically active agent in the composition. In some embodiments, the biocompatible solvent is 5-25% v/v of water. In other embodiments, the biocompatible solvent is 5-25% v/v of DMSO. By adjusting the concentration of polymers and/or solvents, the release of the DMF can be controlled to provide a low initial burst and sustained release of the drug.

In some embodiments, a method of treating a subject with multiple sclerosis (MS) is provided. The method comprises a step of parenterally injecting under the skin of the subject a composition of gellan gum crosslinked with L-cysteine and a medication suitable for MS distributed therein, wherein the medication suitable for MS is releasable from the gellan gum crosslinked with L-cysteine over time, and wherein the gellan gum crosslinked with L-cysteine is biodegradable. In preferred embodiments, the medication suitable for MS is DMF or pharmaceutically acceptable salts thereof. In some embodiments, the gellan gum crosslinked with L-cysteine has a concentration of 0.5-3% by weight based on the total weight of the composition. In some embodiments, the biocompatible solvent is 5-25% v/v of water or DMSO. In preferred embodiments, the gellan gum crosslinked with L-cysteine to the biologically active agent is at a 0.5:1 to 3:1% w/w ratio. U.S. Pat. Application 2019/0380992 describes the effect of dimethyl fumarate (DMF) in MS treatment, incorporated herein by reference. In preferred embodiments, the composition may be parenterally administered (e.g., subcutaneous injection, intravenous injection, etc.). As such, other non-alimentary canal routes of drug administration, such as skin patches which may be in multiple forms including single and multi-layer adhesive forms, matrix forms, reservoir forms that may be attached on the skin, are not used.

The drug delivery implant composition may be administered in one or more effective amounts or doses for treating a particular pathophysiological condition for a sufficient period of time. The term "treatment" or "therapeutic treatment" as used herein refers to bringing a body from a pathological state or disease back to its normal, healthy state. Specifically, unless otherwise indicated, includes the amelioration, cure, and/or maintenance of a cure (i.e., the prevention or delay of relapse) of a disease or disorder. Treatment after a disorder has started aims to reduce, alleviate, ameliorate or altogether eliminate the disorder, and/or its associated symptoms, to prevent it from becoming worse, to slow the rate of progression, or to prevent the disorder from re-occurring once it has been initially eliminated (i.e., to prevent a relapse). It is noted that, this term as used herein may include prophylactic or preventive treatment. The term "effective amount" as used herein refers to an amount that is effective, upon single or multiple dose administration to a subject (such as a human patient) in the prophylactic or therapeutic treatment of a disease, disorder or pathological condition. A "suitable period of time" is defined herein as a sufficient time for a subject to produce antibodies against the administered antigens described herein. A sufficient time for a subject to acquire ability to produce antibodies may be days (e.g., 2, 3, 4, 5, 6 or 7 days), weeks (e.g., 1, 2, 3 or 4 weeks) or months (e.g., 1, 2, 3, 4, 5, 6 months) after a first, second or third dose of the immunogenic composition is administered.

The term "subject" as used herein refers to a mammalian subject. Preferably, it is selected from a human, companion animal, non-domestic livestock or zoo animal. For example, the subject may be selected from a human, mouse, rat, dog, cat, cow, pig, sheep, horse, bear, and so on. In a preferred embodiment, said mammalian subject is a human subject.

The term "pharmaceutically acceptable salt" as used herein refers to the relatively non-toxic, inorganic and organic acid addition salts of compounds as described herein. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobsonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like (see, for example, Berge S. M, et al, "Pharmaceutical Salts," J. Pharm. Sci., 1977; 66:1-19 which is incorporated herein by reference.)

The terms "agent", "medication" and "drug" are used herein interchangeably.

Routes of administration include but are not limited to subcutaneous and intramuscular injections. The subcutaneous administration is particularly preferred. Subcutaneous administration may for example be by injection into the abdomen, lateral and anterior aspects of upper arm or thigh, scapular area of back, or upper ventrodorsal gluteal area. In some embodiments, the compositions of the disclosure are administered in one, or more doses, as well as, by other routes of administration. For example, such other routes include, intracutaneously, intravenously, intravascularly, intraarterially, intraperitnoeally, intrathecally, intratracheally, intracardially, intralobally, intramedullary or intrapulmonarily.

The term "Parenteral injection" as used herein, refers to an injection intended to be administrated through the human or animal body, either by direct injections, for example, bolus intravenous (IV), intramuscular (IM) or subcutaneous (SC) or by infusion with a controlled infusion rate or by direct implantation through IM or SC. The injection formulation is formed to be sterile and pyrogen-free, clear or practically exempt of visible particle and to be free from sub-visible particles as required by pharmacopeias EP, USP and JP, shows no evidence of phase separation for the emulsions, or aggregates formation for aqueous dispersions such as injectables Mab (monoclonal antibody) preparations. The suspension of the formulation also contemplates the use of appropriate particle size and any sediment should be readily dispersed upon shaking to give stable formulations and ensure the correct dose to be withdrawn and injected. Parenteral preparations may require the use of excipients that should be biocompatible, be selected for the appropriate use and to be included at the minimum efficient concentration. The functionality of these excipients includes making the preparations isotonic with respect to blood (e.g., glucose/dextrose, mannitol, sodium chloride, etc.), adjusting the pH to the physiological components (e.g., mineral or organic acids or salts), preventing the degradation of the drug substances, ensuring or increasing the drug substance's solubility, and providing adequate antimicrobial preservative property. The excipients should not adversely affect the intended medicinal action of the drug.

Example 1

Materials and procedures used to generate an exemplary drug delivery polymer composition are described herein. Dimethyl fumarate (DMF) and gellan gum (GG) were purchased from Sigma Aldrich, Mumbai. DMSO (Dimethyl sulfoxide) and (BA) (benzyl alcohol) were purchased from research & laboratory chemicals. Acetonitrile of HPLC grade and Benzyl benzoate (BZ) were procured by the Ranchem Limited. All the required chemical reagents involved in the study were analytical standard parameter grade.

Preparation of Cross-Linked GG with the L-Cysteine 1 gram of GG was taken into a 150 ml of RBF flask and was dissolved in 15 ml of acetone. Then 2 ml of thiol chloride was added to the GG and acetone mixture and further mixed for 15 min. After 15 min, the amino acid type l-Cysteine were put to the mixture and blended for 1 hr. The completion of reaction was confirmed by TLC.

Injectable In Situ Gel Preparation

The method employed to formulate in-situ gels includes homogenization method. 25 ml of water was taken and heated to 80° C. Addition of the polymer and the 250 mg of the Dimethyl fumarate was followed. The prepared mixture was blend for at least 10 min at 80° C., resulting in a uniform distribution of the drug and the polymer. After stirring the solution was cooled and the solution was transferred to the 25 ml screw tight cap bottle. The formulation chart is shown in the Table 1.

TABLE 1

Formulation chart of Injectable in-situ Gel

| SI No | Formulation Code | Conc (% w/w) | Drug (mg) | Solvent DMSO | Water |
|---|---|---|---|---|---|
| 1 | A1 | 0.5 | 250 | 25 | 0 |
| 2 | A2 | 0.5 | 250 | 25 | 0 |
| 3 | B1 | 0.75 | 250 | 25 | 0 |
| 4 | B2 | 0.75 | 250 | 25 | 0 |
| 5 | C1 | 1 | 250 | 25 | 0 |
| 6 | C2 | 1 | 250 | 25 | 0 |
| 7 | D1 | 1.5 | 250 | 0 | 25 |
| 8 | D2 | 1.5 | 250 | 0 | 25 |
| 9 | E1 | 2 | 250 | 0 | 25 |
| 10 | E2 | 2 | 250 | 0 | 25 |
| 11 | F1 | 3 | 250 | 0 | 25 |
| 12 | F2 | 3 | 250 | 0 | 25 |

The injectable form of ISFI was characterized as described herein. Drug and polymer can interfere when preparing ISFI because both are in adjacent with each other that can contribute to drug instability. The compatibility between the dimethyl fumarate and cross-linked polymer were determine by the FTIR (Fourier Transform Infra-red spectroscopy) and DSC (differential scanning calorimetry). KBr pellet principal and method 6000 kg/cm$^2$ were applied to obtain the spectra of all developed formulation and with the powder diffuse reflectance in the range of 400-4000 cm$^{-1}$ on FTIR. (8033-USA model, Shimadzu).

By using Schimadzu-thermal analyzer DSC-60 made in Japan, all the possible chances of interactivity and changes between dimethyl fumarate (DMF) & polymer, DSC thermograms of drug, polymer, physical mixture and prepared ISFI were calculated. Samples were mounted in alumina crucible, thermograms was achieved at a rate of 10° C./min of scanning with the flow rate of 10 ml/min, performed in the liquid nitrogen atmosphere across the temperature of 30-300° C.

$^{13}$C Solid-State Nuclear Magnetic Resonance Spectroscopy ($^{13}$C-CP/MAS NMR)[35]

$^{13}$C-CP/MAS NMR for all samples were performed at 75 MHz by using BRUKER instrument 300. For all materials were spun at the 4.5 kHz magical angles, and the cross-polarization pulse pattern was used. The time for pulse reiteration was for the period of 3 second while 1 ms for the contact time and usual accumulation scan for every sample was approx. 1100.

Evaluation of the Cation-Dependent In Situ Gelling Properties

The injectable form of ISFI was evaluated as described herein. During the process of GG-Cys conjugate hydration and control (GG) in demineralized water, the disulfide bonds development was eluded by regulating the pH to pH 4.0 with 1 M HCl. Lastly, the pH has been steadily changed to 7.0 with 0.33 M NaOH. Later, concentrations of physiological cation present in tear fluids have been applied to a different concentration of polymer solutions like $Na^+$ ions of 142 mM, $K^+$ ions of 19 mM, and 0.6 mM of $Ca^{2+}$ ions. Subsequently, by using stress sweep with rheological oscillatory estimation and a cone-plate Brookfield viscometer (DVII+ viscometer) G', G", |η*|, and tan δ were measured. The angular rate was maintained continuously and the shear stress from 0 to 100 Pa was escalated. With the help of GG-Cys/GG improvement ratios of G', G" and |η*| were calculated and tan δ by GG/GG-Cys. All of the prepared formulations were filled in the 25 mL of the glass bottle. The bottle was kept in front of the clarity testing port under the black and white background to observe the presence of any visible particulate matter.

Gelation time and viscosity were determined. Test tube inverting technique was used to calculate the gelation time. In the deionized water the GG powder were dissolved at 70° C. for 5 min by vigorous shaking. This homogeneous solution was then kept for cooling till the room temperature is attained. Then potassium chloride (KCl) solution of appropriate concentration was added. Finally, the prepared formulation was kept under observation to check the time required for the GG solution to turned into a gel. The state of sample and test tube were observed on every 5 sec. By using the nonflow and flow benchmark the gelation time were determined. Viscosity studies of all the formulations were measured by using Brookfield DVII+ viscometer using spindle LV3 at the rpm of 50. Measurement of viscosity was possible at 37±1° C. using a thermo stated water jacket.

The content of drug was determined. Drawing 2 ml of gel in the volumetric flask having a capacity of 10 ml and the volume makeup with methanol were used for drug content analyses present in prepared drug development. 0.1 mL solution was pipetted out and put into another volumetric flask of 10 mL capacity from the above prepared solution and methanol were used for volume makeup. Absorbance was measured at 212 nm.

Syringeability test was performed. Gel packed in 5.0 ml glass syringe with pan resting on the piston and kept at 5±1° C. The developed device was used for evaluating the syringeability of the gels. Syringe were fastened to aid with a 18 G needle. This pan was massed by 0.5 kg and was used as a period of syringeability when the gel had to be expelled, this required time consider as syringeability time.

Optimization of the prepared formulation using DoE software was performed. The design-based formulations developed and evaluated with the software package of Design Expert® ver 8.0.1. Statistically, the activity of the drug formulation variables with the response variables were measured by one way ANOVA at the level of 0.05. (Daniel, 1983). By using the following polynomial equation of response surface method, the design was assessed.

$$Y = \beta_O + \beta_1 X_1 + \beta_2 X_2 + \beta_3 X_1 X_2 \ldots$$

where response variable presented by Y, $\beta_O$ represent the constant and the regression coefficients denoted by $\beta_1$, $\beta_2$, and $\beta_3$. Primary action was represented by X1 and X2, X1X2 demonstrate how the outcome alters if two variables are modified concurrently (Singh, 2005; Singh, & Ahuja, 2004). The equation was developed by one-way ANOVA and multiple linear response analysis for every response parameter (Daniel, 1983). Backward elimination processes created the predictor equation that consist just significant terms (Kapoor et al., 2012).

In-vitro drug release study was performed as described herein. The in vitro release study of Dimethyl Fumarate from injectable in situ gels was carried out at 37° C. with 100 ml of pH 7.4 phosphate Buffer. Formulation equivalent to 50 mg of drug was placed into a cellophane membrane. The membrane was hydrated prior to use and wrapped to form the pocket of gel. This pocket of membrane was then placed in the phosphate buffer. At previous established time interval, 1 mL medium were collected & replenished by the freshly prepared medium of 1 ml. The release amount of Dimethyl Fumarate was analyzed at 212 nm by UV spectrophotometer.

In vivo drug release study was also performed. Albino Wistar rats (275-300 g) were used in the study. Sterile polypropylene cages with paddy husk were used for the housing of experimental animals. Standard food pellets were given to the animals with water ad libitum. Uses of experimental animal were approved by the IAEC (JSSCP, S. S. Nagar, Mysore, India Code No: 132/2013) and for all the purpose of animal welfare the CPCSEA guidelines were followed.

The experimental animals were separated into groups of three and each group consisted of three animals. First group received solution of Dimethyl Fumarate in saline by SC route and group II were injected with optimized injectable in situ gel by SC, and the group III was injected with blank injectable in situ gel by SC. For injecting 0.5 mL of injectable gel, a syringe of 1 mL with the needle of 26-gauge was used.

For the In-vivo detection of Dimethyl Fumarate, an aliquot of blood was drawn from retro orbital sinus of each rat at specified blood collection times. 1.5 mL aliquot of blood from retro orbital sinus was collected in an EDTA coated Eppendorf tube. The tubes were centrifuged at 4° C. and 8000 rpm for 10 min to collect plasma. Plasma was separated into a separate eppendorf tube. Until the screening or assay of plasma samples by using HPLC, the sample was stored at −20° C.

Tissue biocompatibility study of DMF ISFI system was performed. Mice were separated into three groups i.e., positive control group, test group, negative control group and each group consist of three animals to assess the DMF and ISFI biocompatibility. All of the three groups received different drugs like first group received phosphate buffer of pH 7.4 dispersed DMF, test group was given both drug DMF with the ISFI and the last group were given only ISFI. For all physical signs of inflammation, all the animals were visually observed. Produces responses in experimental animals were graded as 0 for normal, + for mild symptoms, ++ for moderate and +++ used for the severe symptoms. After injecting the drugs in animals, one mouse per group was sacrificed at the interval of $3^{rd}$ day, $7^{th}$ day and $14^{th}$ days. The adjacent tissues were excised and fixed in 10% formalin tamped with phosphate buffer. The tissue was under the observation of optical microscope after the hematoxylin and eosin staining process for the changes in acute inflammatory responses, fibrosis and foreign body reaction. (Anderson and Langone, 1999 and Park and Park, 1999).

Fourier Transform Infrared Spectroscopy (FT-IR)

DMF and in situ forming implant were subjected to spectroscopic analysis (FT-IR) for the testing of compatibility to confirm that was there any interactivity possibilities between the used drugs and polymers. Observed DMF spectra with the aid of IR and loaded drug in situ gel were found to be nearly identical. The standard drug FT-IR spectra and the spectra of formulated drug showed that no alteration was found in the DMF peaks characteristics.

Therefore, no evidence was found for the drug and polymer chemical interaction. The obtained spectra are shown in FIG. 1.

The research of differential scanning calorimetry (DSC) was performed on pure drug and all of the formulations. Stability of the drug formulation was confirmed by the DSC thermogram obtained from the pure drug and formulation showed no significant shift in the endothermic peak. Table 2 represents the pure drug DSC and prepared formulation.

TABLE 2

DSC data of pure drug and formulation

| Sample number | Drug and formulation | $T_0$ ° C.[a] | $T_m$ ° C.[b] | $T_c$ ° C.[c] | Melting Range ° C. |
|---|---|---|---|---|---|
| 1 | Pure Drug | 101.5 | 103.38 | 106.7 | 5.2 |
| 2 | Formulation | 98.2 | 101.1 | 105.9 | 7.7 |

Figure 2A:
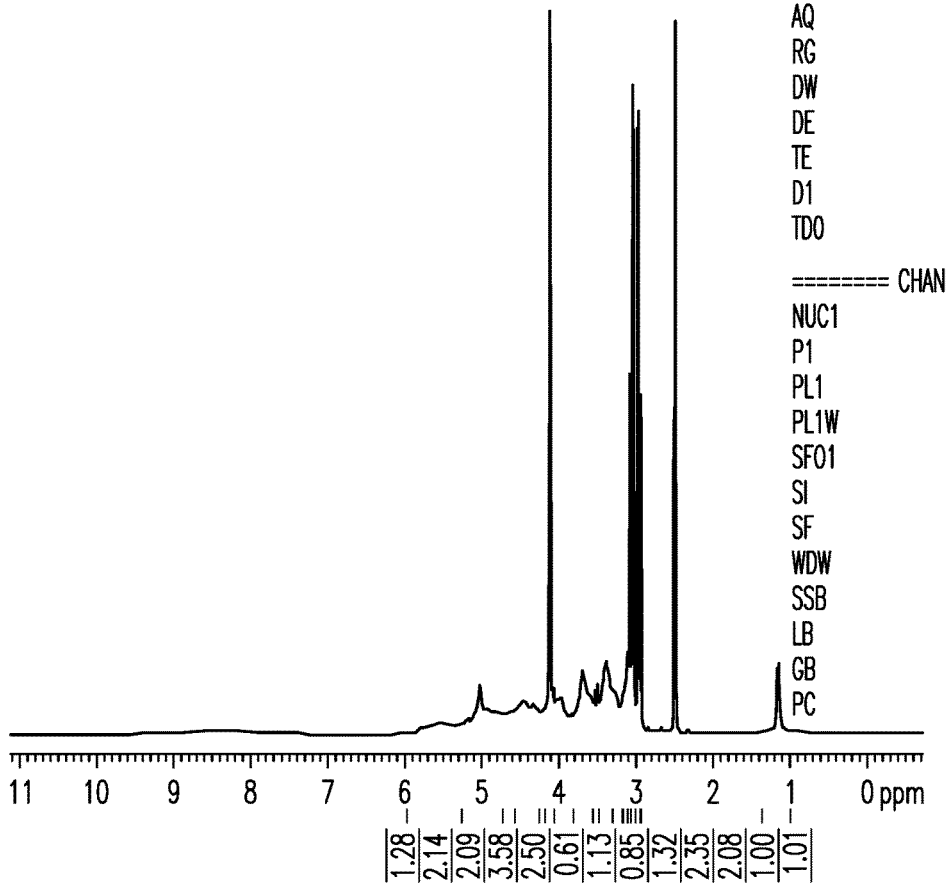
FIG. 2A-B show (A) NMR of the cross-linked gellan gum with the L-Cysteine and (B) FTIR of the Gellan Gum, L-Cysteine and the crosslinked gellan gum.
Figure 2B:
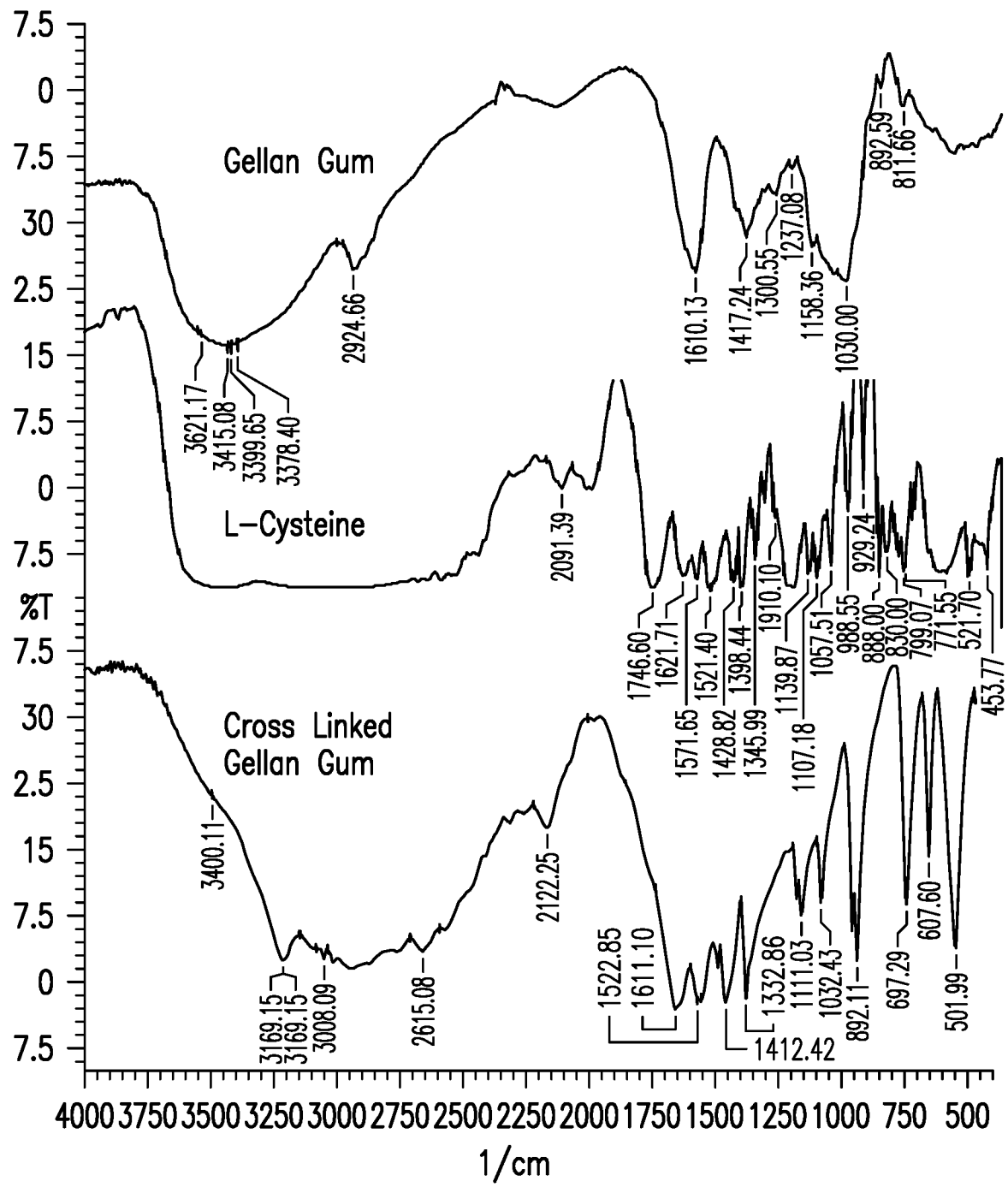

[a]$T_0$ ° C. - Onset of melt
[b]$T_m$ ° C. - Melting point
[c]$T_c$ ° C. - Completion of melt The crosslinking of GG and L-cysteine was confirmed by NMR and FTIR spectra. For NMR spectra, the absorption peak at δ value of 5.514 with the integration value of 1.28 represents amide linkage conforming that the major amino group immobilized the cysteine to the GG carboxylic acid which is indicated in FIG. 2A. Since there is no proton peak at the δ value of >9 which is required for 'SH' mercapto proton, the crosslinking of gum and amino acid has taken place. FTIR data also conformed the crosslinking of the GG with the L-Cysteine. In the spectra, it can be seen that the peak of NH group at 3400 cm$^{-1}$ and H—C=O group at the 2615.08 cm$^{-1}$ have formed, confirming the crosslinking of gum and amino acid (shown in FIG. 2B).

To evaluate the cation dependent in situ gelling properties, the oscillatory stress sweep was used for the determination of storage modulus, loss modulus, and complex viscosity after putted the cations in 1.0% polymer solutions. Results showed that GG cations-dependent in situ gelling characteristics were not only preserved but even enhanced by cysteine immobilization upon this polymer. According to Table 3 with the comparison of the unthiolated polymer, G' were enhanced 224.2-fold, G" were enhanced 2.7-fold and |η*| were better to 9.4-fold. The GG were a sole with a tan d of 62, while the reformed polymer with a failure tangent of 0.17 was a solid gel on this concentration.

The property of cations was supported the GG solution gelation mechanism, and monovalent cations cannot endorse the gelation as considerable affectively promoted by the divalent cations. The accumulation of double helix was benefited with shielding the electrostatic repulsion by monovalent cations. Whereas, with the reaction of carboxylic acid at the different gellan chains ionic bonds were form straight by the divalent cations, resulting by the inter-chain bridging the double helices that were accumulated. (Dai et al., 2010; Ogawa et al., 2006).

When $Ca^{2+}$ was applied to the aquatic GG solutions, it was found to provide much stronger gelation and caused a denser filling structure in the critically modified gel after $K^+$. GG gelation in water solution has until now been widely researched and a two-step mechanism of this gelation has been established. A first move is to alter the configuration of a random coil into a double helix, while the second stage is to add the double helices to make junction points, which ultimately results in gelation. (Chandrasekaran et al., 1988; Crescenzi et al., 1986; Nakajima et al., 1996; Skjåk-Bræk et al., 1989).

The finding of prepared formulation of injectable in situ gel was clear and transparent under black and white backgrounds with the help of clarity testing port. There was no sign of any visible particulate matter in all the formulations. It was concluded that the added polymers are suitable to produce a clear preparation.

Figure 3A:
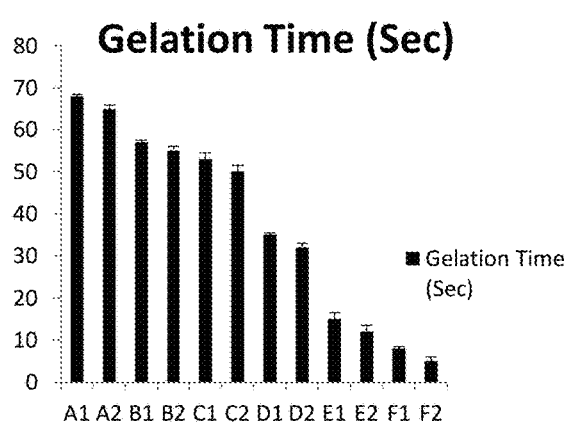
FIG. 3A-C show (A) gelation time of the prepared composition of the present disclosure, (B) viscosity of the prepared composition and (C) syringeability of the various formulations.
Figure 3B:
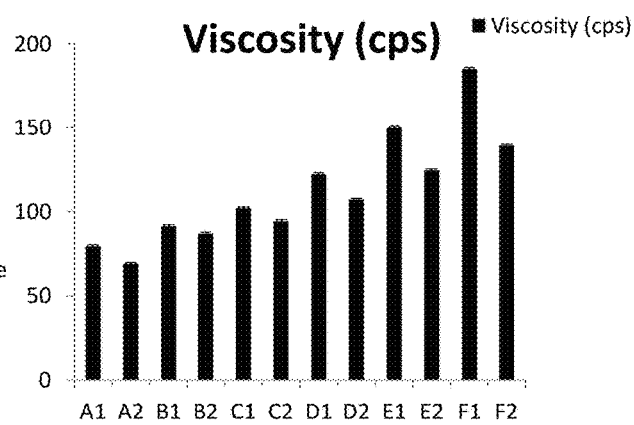
Figure 3C:
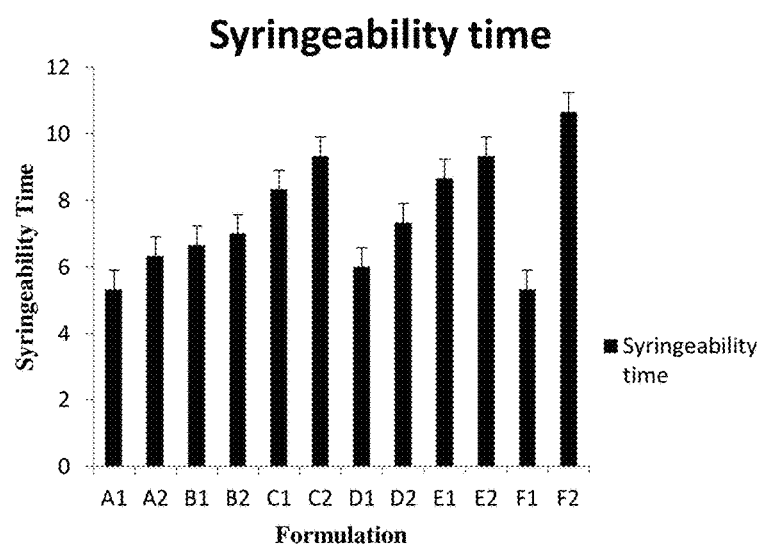

The Gelation time and viscosity for the formulations are shown in FIG. 3A-C. From the data it can be observed that GG is inversely proportional to gelation time. So, when the GG concentration increases there was found to be decreased in the gelation time. Because as the concentration of GG increases interaction of the polysaccharide chain with the cation present in the solution increases. Whereas in the 0.5% solution the gelation time is more because the GG molecule are far from each other and the cation take time to interact with the suspended molecule of the GG (Dai et al., 2010). The formulation prepared in the water (solvent) shown less gelation time when compared to the formulation prepared with the DMSO because the cation gets easily dispersed in the water, so it quickly reacts with the GG molecule. When the concentration of the GG increases the viscosity of the formulation increases this was due the increases interaction of the polysaccharide chain.

All of the in situ gels were syringeable by the needle of 18 gauze and it was clearly explained in the conclusion of syringeability study. After that, recorded syringeability time were found between 5.33±0.58 to 10.66±0.58 sec which is shown in FIG. 3C. Formulation A1 recorded the lowest syringeability time of 5.33 sec and formulation F2 with 10.66 sec, the highest. In-situ gels were easily syringeable when a constant weight (force) was applied and syringeability time was only dependent on viscosity of in situ gels. Other test parameters were kept constant during the study. From the data, it can be inferred that the syringeability time is directly proportional to the viscosity. The syringeability of F2 prepared formulation was found to be 10.66±0.58 sec which may be attributed to its greater viscosity and formulation A1 syringeability were found to be 5.33±0.58 sec because of its less viscosity. The period of syringeability were dependent mostly on viscosity of gel due to polymer concentrations.

Figure 4:
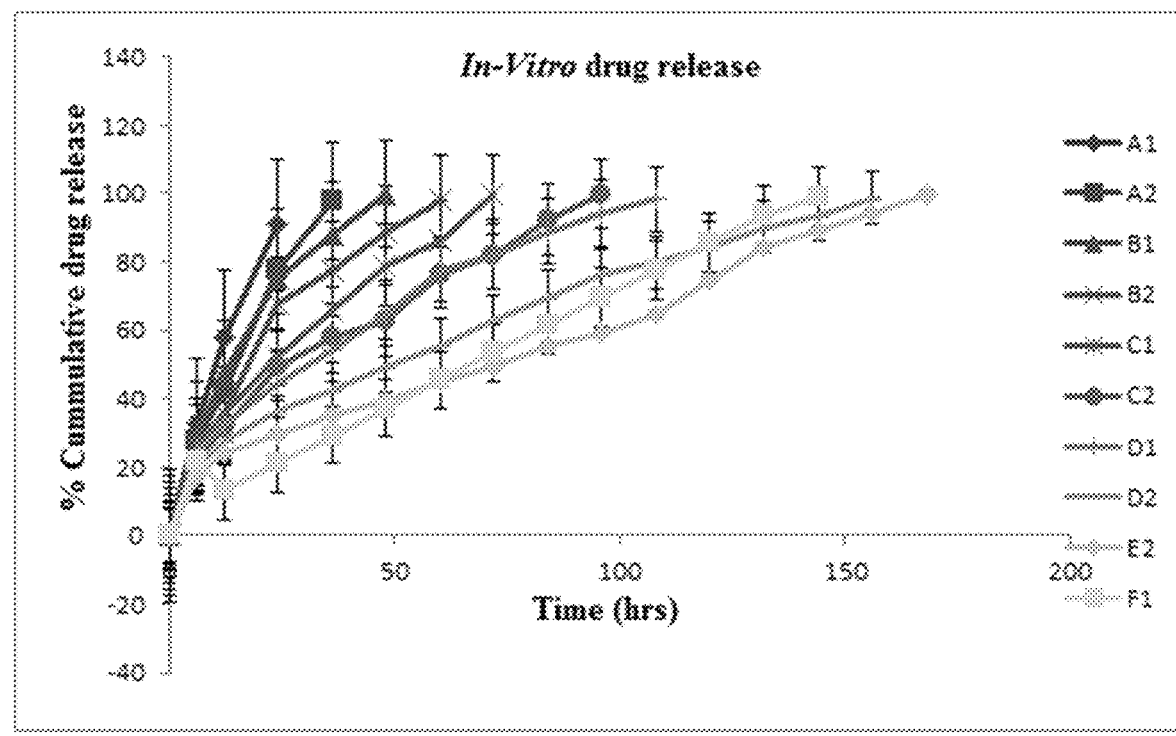
FIG. 4 shows in vitro drug release of the composition of the present disclosure.

All prepared formulation were undergone for in-vitro drug release studies in the pH 7.4 phosphate buffer at the temperature of 37±0.1° C. FIG. 4 showed diffusion and erosion in-vitro drug releases formulations. Studies of in vitro release of drugs have shown that polymer and solvent (water and DMSO) amounts have affected the release of the drug from formulations. Drug discharge from the formulation were retarded by increasing the polymer concentration. This is due to the fact that more the concentration of the GG in solution more will be the viscosity of the solution, it was already seen in GG that when concentration will be increases the viscosity will also increases and is due to an increasing association between the chain and the polymer concentration. Another reason can be the altered configuration of a random coil into a double helix and adding the double helices to make junction points which results in drug release from the matrix of polymer were delayed.

Water and DMSO effect on the release of drug was also observed and it was found that in presence of water, the cross-linked polymer swells due to the hydration of the polymer leading to more diffusion length for the drug while in DMSO there is no hydration of the polymer. From the FIG. 4, it can be seen that there is burst release from the formulation because due to quick distribution of the medication between fluid formulation injection and firm implant forming during lag time. The splash influence in formulations with great polymer concentrations has been shown to be smaller as great polymer concentrations appear to rise systems viscosity and therefore slow down drug removal to the medium.

Rise in total viscosity of the product can lead to the retardant effect of these polymers as well as to the delay in the drug release procedure in distorting or squeezing of the extra-micellar aqueous channels of GG matrix. More gel intensity or molecular contact between the drugs and polymers may also slow drug delivery. In FIG. 4, it showed that the formulation A1 shows the release (91%) till 24 hrs, while formulation A2 and B1 shows drug release (97.8% & 99.8%, respectively) till 36 hrs and 48 hrs, whereas C2 shows drug release (99.7%) till 96 hrs. Moreover, the viscosity of the cross-linked GG increases so this also affects the drug release rate. From the data shown in FIG. 4, it can be concluded that the formulation E2 provides 99.8% drug release till 168 hrs and having the optimum viscosity and the gelation time and the Syringibility.

From the result it can be concluded that amongst all the prepared formulation F2 showed retarded drug release. Whereas E2 preparation showed better result than F1. But due to the high viscosity of F1, it is not suitable as injectable formulation and having the more Syringibility than the E2 this is because of the concentration of the polymer in the formulation. After the preliminary break of the DMF in starting 6 hours, it was observed that the release rate of all DMF formulations increased continuously and constantly for the next 44 hours. Although the profile of release drug tends to be identical and nearly linear in the second step, the quantitative increase and variance between different formulations remains significant and drug release has also been assessed for goodness-of-fit to evaluate the release kinetics of the formulations in many statistical model equations. The variables R2, k and n of the analytical model equation showed that most formulations were Higuchi and Peppas. The findings suggested drug release by diffusion based mostly on n values of the Peppas model, whether by fickian or by anomalous transport. ($0.5 < n < 1$).

The design-based formulations developed and evaluated with the software package of Design Expert® ver 8.0.1. Statistically, the ANOVA of one-way method were used at the 0.05 level for measured the variables of drug formulation with the response variables activity (Daniel, 1983). By using the following polynomial equation-1 of response surface method, the design was assessed, $$Y = \beta_O + \beta_1 X_1 + \beta_2 X_2 + \beta_3 X_1 X_2 \ldots \quad (1)$$

where the response variable presented by Y, $\beta_O$ represent the constant and the regression coefficients denoted by $\beta_1$, $\beta_2$, and $\beta_3$. Primary action was represented by X1, X2 and X1X2 demonstrate how the outcome alters if two variables are modified concurrently. The equation was developed by ANOVA one-way method and multiple linear response analysis for every response parameter (Singh et al., 2005; Daniel, 1983). Backward elimination processes created the predictor equation that consist just significant terms.

Table 4 represents the variables response values, which acquired from the prepared lots according to surface design of I-optimal response, where Y1 (% released drug, 24 hours), Y2 showed (% released drug, 48 hours), Y3 present (% released drug, 96 hours) and Y4 represent the viscosity. The layout was analyzed using a linear surface response model based on p-values method, fit test lacking model, modified R2 and anticipated R2 to determine the significant design conditions and their relations and their effects on response variables Y1, Y2, Y3 and Y4. ANOVA developed linear polynomial pattern equations. The r2 value for linear model was similar to 1.000 and suggested that polynomials of the surfaces were outstanding for the data of variable response. Picked model validity expressed by the significant value and it has been found that the entire lack of fit values were significant ($p > 0.05$). The similarity of R2 and foretold $R^2$ to the real model R2 suggested the suitability of the data as well. The values of X1 and X2 were found to be significant ($p < 0.0001$). Finally, for every single variable response of polynomial equation of first order were acquired form significant coefficient terms as listed below:

$$Y1(\text{Release 24}) = 42.93 - 30.27*A + 2.74*B - 2.03*A*B \quad (2)$$

$$Y2(\text{VISCOSITY}) = 122.76 + 43.54*A + 11.38*B + 9.91*A*B \quad (3)$$

$$Y3(\text{Release 48}) = 59.69 - 32.46*A + 4.28*B - 1.07*A*B \quad (4)$$

$$Y4(\text{Release 96}) = 82.93 - 18.71*A + 3.58*B + 1.71*A*B \quad (5)$$

There has been no reported interaction terminology like X1 X2 in the Eqs model. (1)-(4), if there were any significant values found between the model term then those were excluded. In general, the findings received by model test revealed that the design, variables, levels, and responses selected are acceptable and relevant.

TABLE 3

Storage modulus G', Loss modulus G", Complex Viscosity | η* |, and loss tangent tanδ of 0.5% GG-Cys conjugate and 1.5% unmodified GG.

| PARAMETER | GG | GG-Cys | IMPROVEMENT RATIO |
| --- | --- | --- | --- |
| G' (Pa) | 3.4 ± 3.9 | 762.4 ± 171.4 | 224.24 |
| G" (Pa) | 46.3 ± 35.1 | 126.8 ± 13.6 | 2.74 |
| \| η* \| (Pa · S) | 13.1 ± 5.6 | 123 ± 27 | 9.89 |
| tan δ | 62.043 ± 61.7 | 0.172 ± 0.04 | 360.72 |

$^a$Mean ± S.D., n = 3.

Figure 5A:
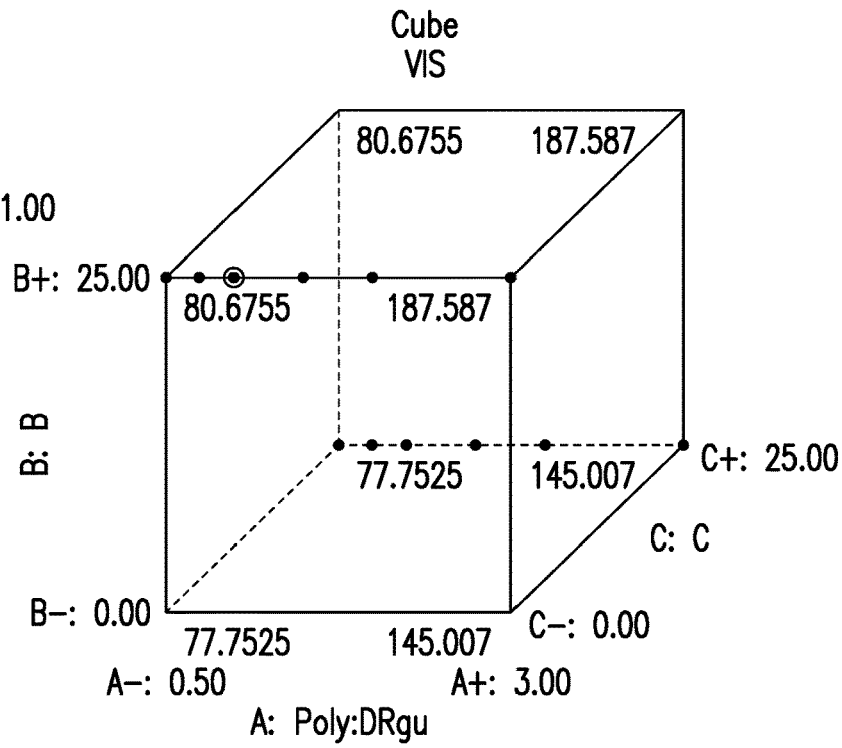
FIG. 5A-D show the effect of (A) 1% w/w polymer concentration in DMSO or (B) 2% w/w polymer concentration in DMSO on the viscosity of the formulation and the effect of (C) 2% w/w polymer concentration in water and (D) 3% w/w polymer concentration in water on the viscosity of the formulation.
Figure 5B:
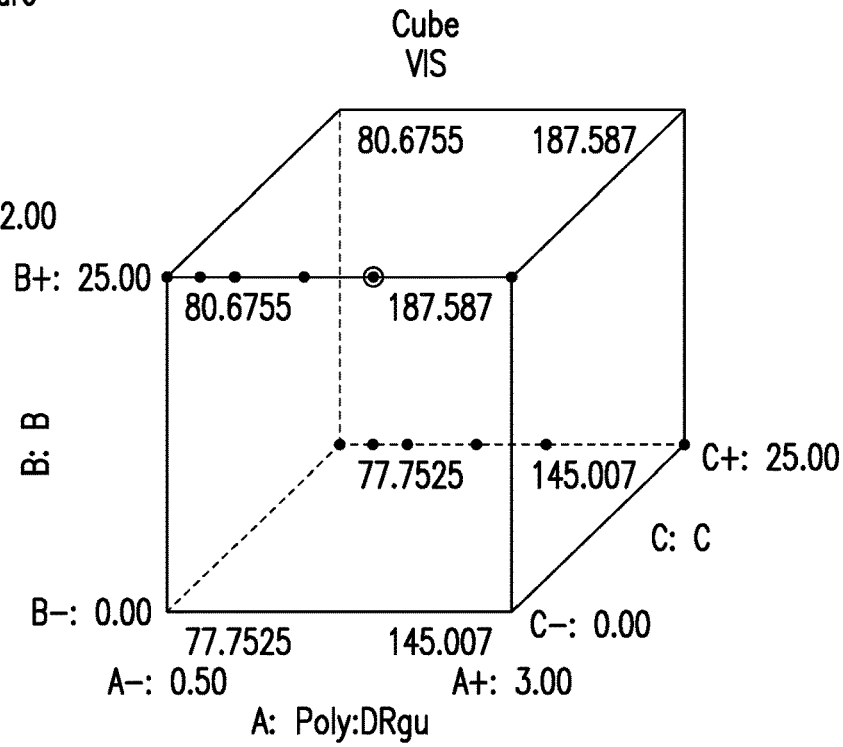
Figure 5C:
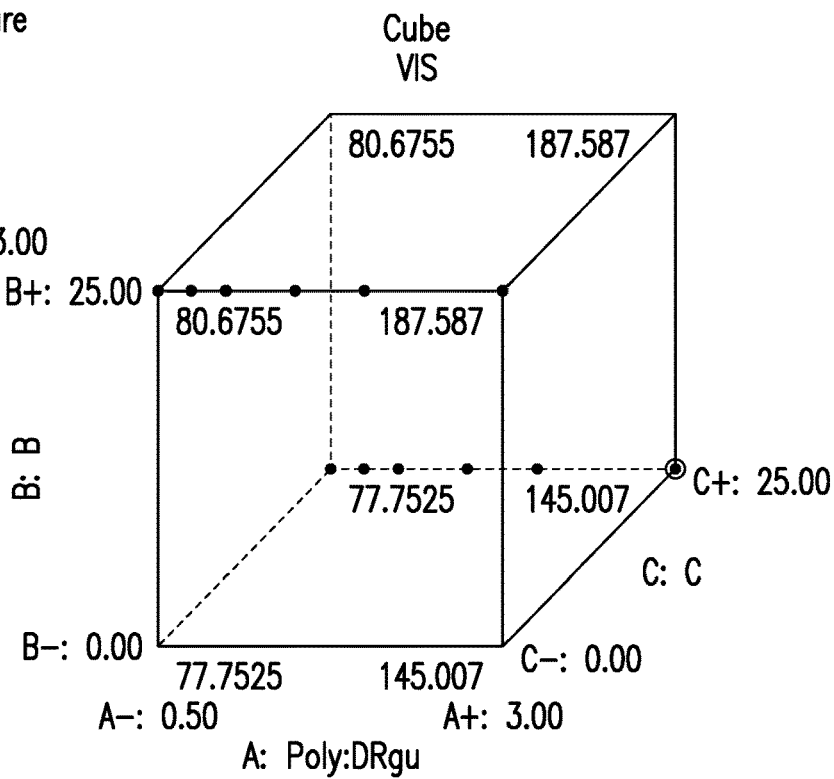
Figure 5D:
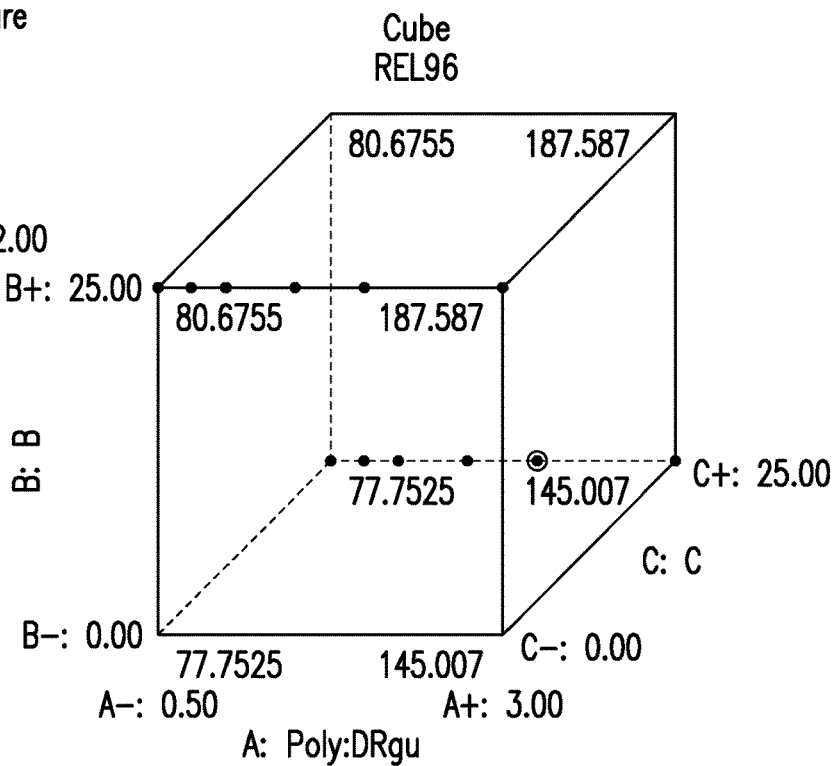
Figure 6A:
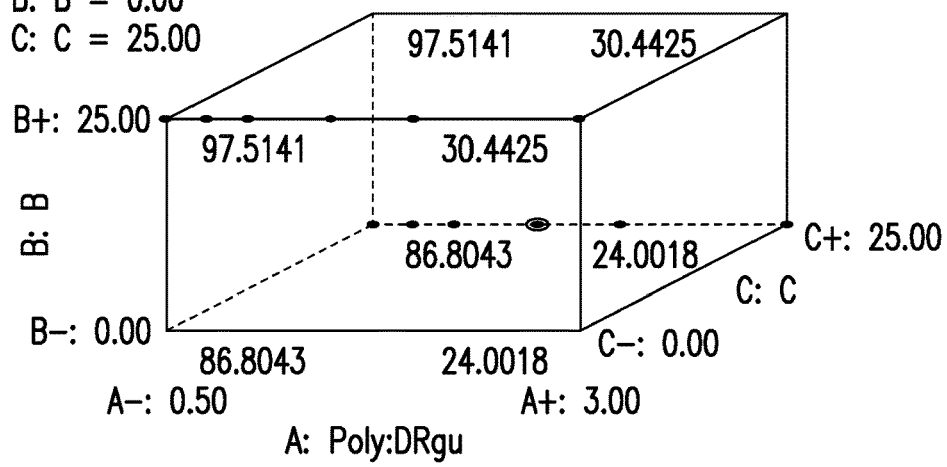
FIG. 6A-D show the effect of 1.5% w/w polymer concentration in water with (A) 48 hr and (B) 96 hr release and the effect of 1.5% w/w polymer concentration in DMSO with (C) 48 hr and the (D) 96 hr release.
Figure 6B:
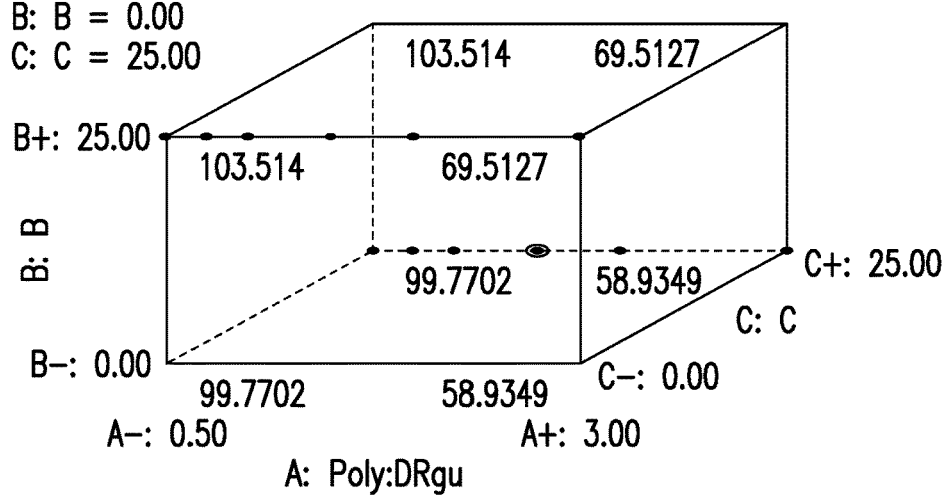
Figure 6C:
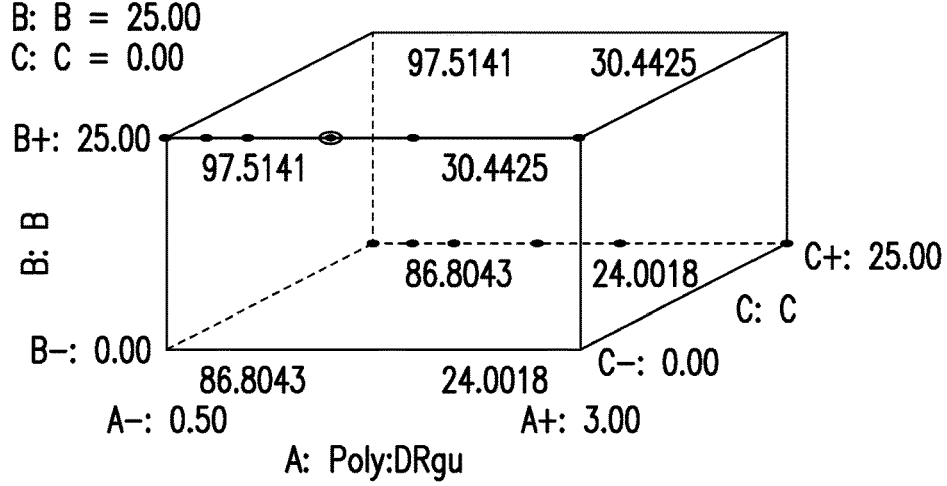
Figure 6D:
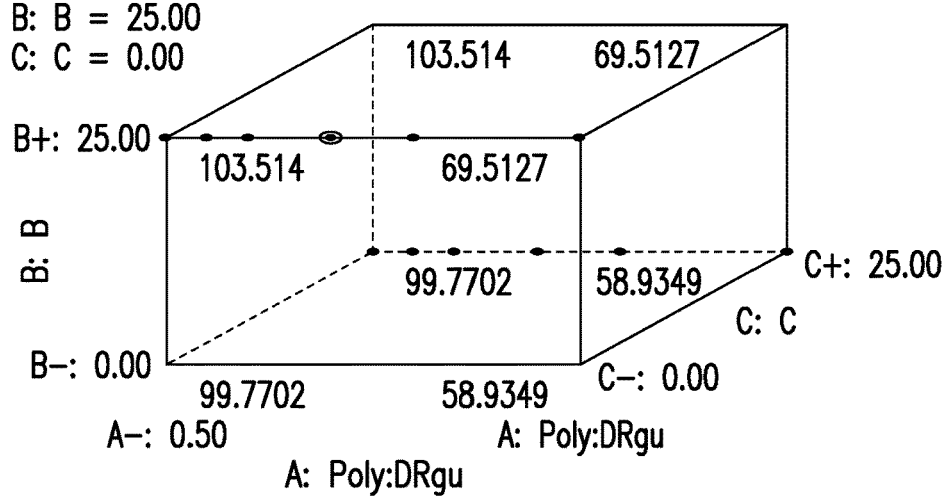
Figure 7A:
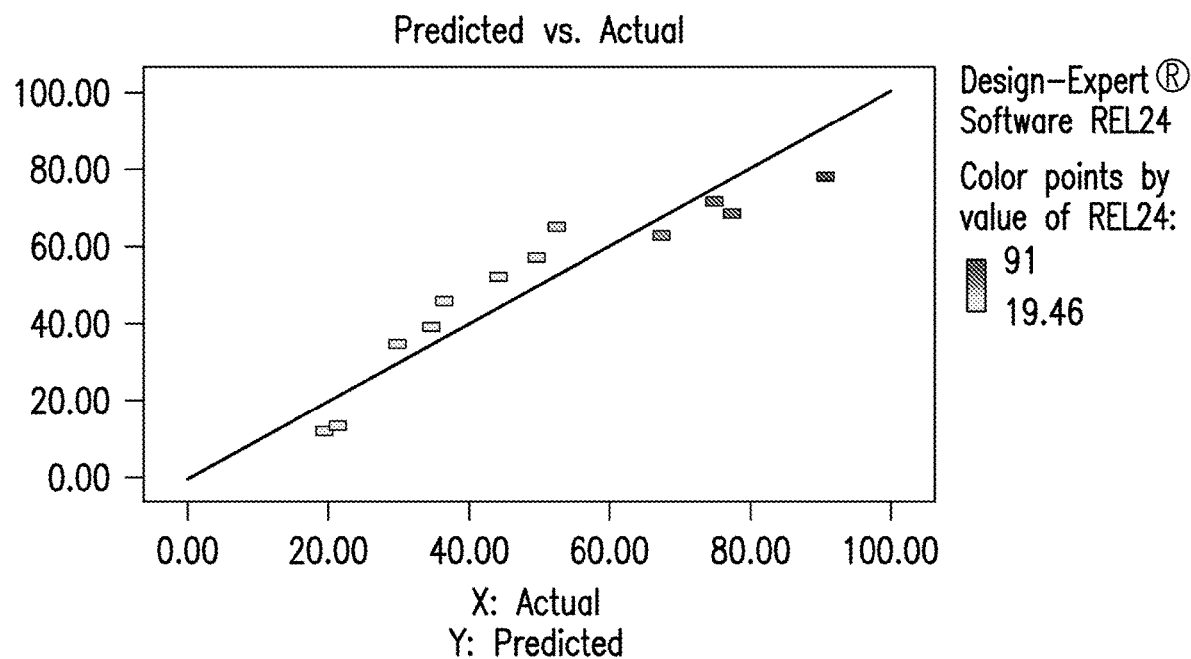
FIG. 7A-D show the comparisons of the actual release value and the predicated release value in conditions including 1.5% w/w of polymer in water with (A) 48 hr and (B) 96 hr release and 1.5% w/w of polymer in DMSO with (C) 48 hr and the (D) 96 hr release.
Figure 7B:
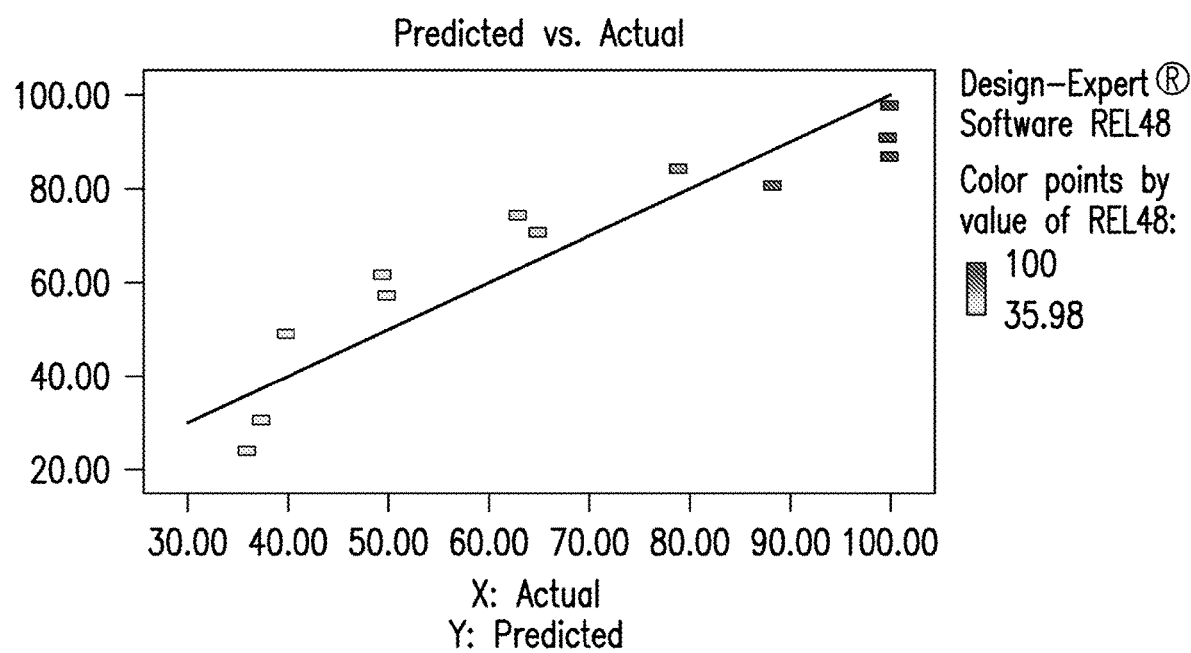
Figure 7C:
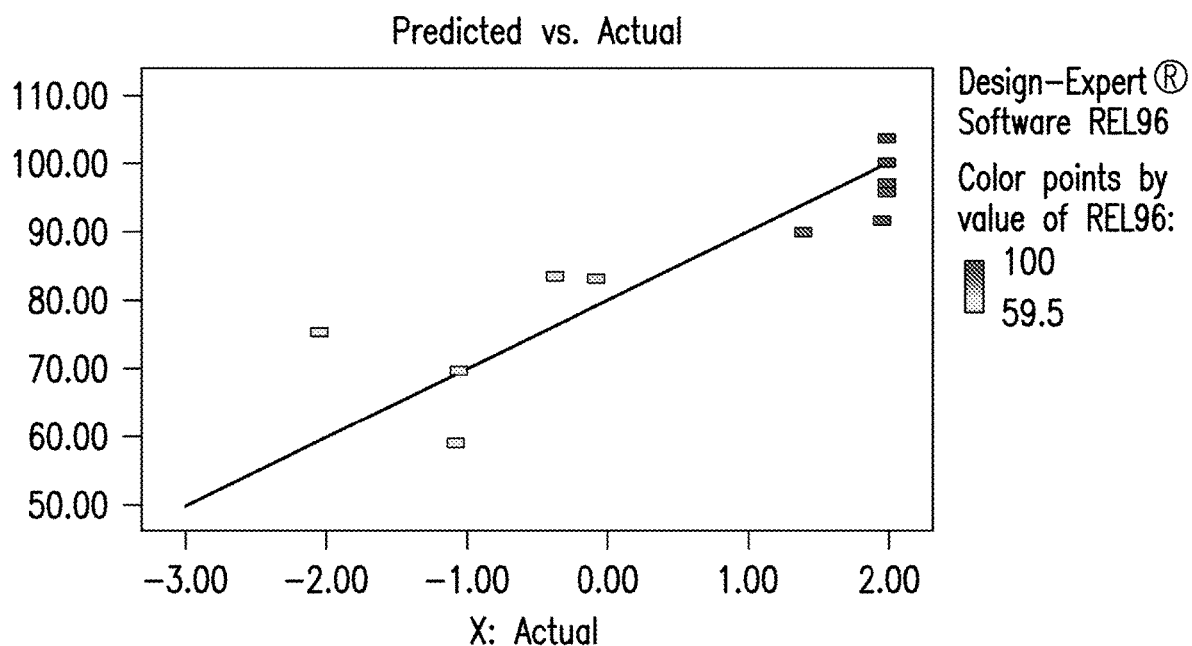
Figure 7D:
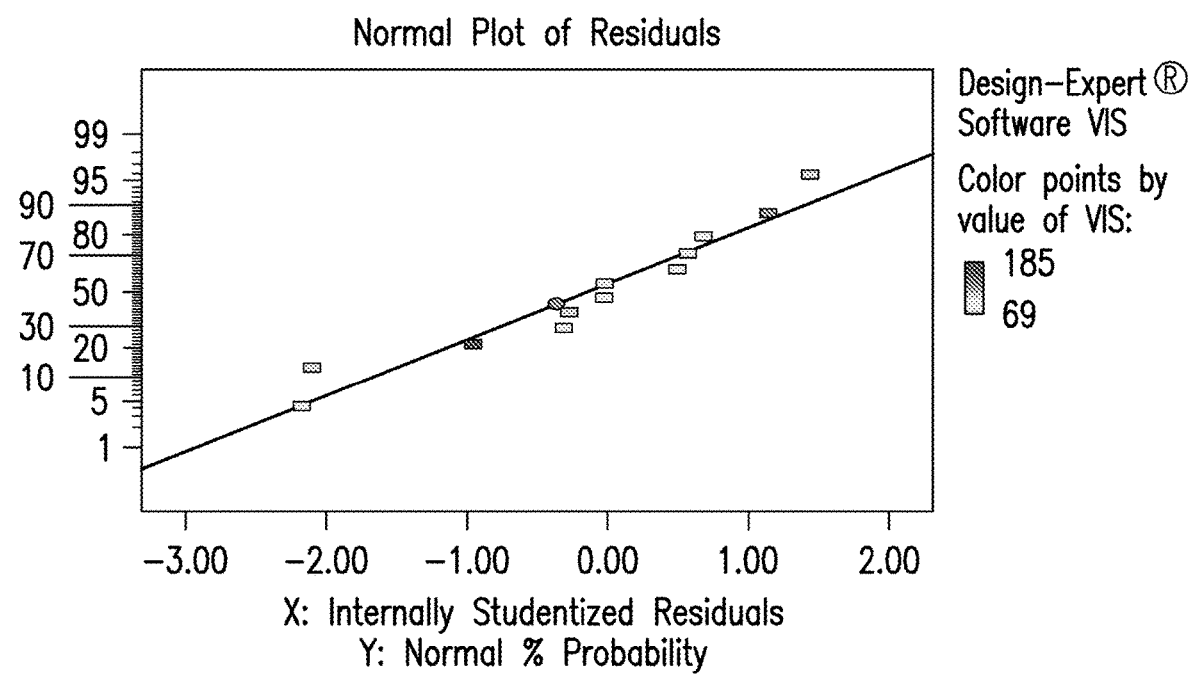

The effect of amount of polymer on the prepared formulation viscosity i.e., as increases in the amount polymer the formulation viscosity also increases this can be attributed due to more polysaccharide interaction at higher concentration which increases resistance to flow. From FIG. 5A-B, it is shown that at 1.0 and 2.0% w/w in DMSO concentration of the gum the viscosity of the formulation was 102, 150 cps respectively. FIG. 5C-D show that at 2.0 and 3.0% w/w in water concentration of the gum the viscosity of the formulation was 124.6, 139.3 cPs respectively. From FIG. 5A-D, it can be seen that the actual value and the predicted value for the viscosity is almost coming in the straight line concluding that the prepared formulation is significant.

Table 4 shows that polymer concentration effect and solvent on the discharge of the drug from the prepared formulation i.e., as the polymer concentration increases the release of the formulation is decreases this can be attributed due to more viscosity at higher concentration, making drug to move slowly and drug get trap within the matrix of polymer.

TABLE 4

Design of the prepared formulation

| Run | Formulation | Block | Factor A: Polymer (%) | Factor B: Solvent | Response 1: 24 hr | Response 2: 48 hr | Response 3: 96 hr | Rsponse 4: Viscosity |
|---|---|---|---|---|---|---|---|---|
| 1 | A1 | Block 1 | 0.5 | DMSO | 91 | 100 | 100 | 79.46 |
| 2 | B1 | Block 1 | 0.75 | DMSO | 75.2 | 99.8 | 100 | 91.33 |
| 3 | C1 | Block 1 | 1 | DMSO | 52.6 | 78.9 | 100 | 101.96 |
| 4 | D1 | Block 1 | 1.5 | DMSO | 44.4 | 64.9 | 94.1 | 122.2 |
| 5 | E1 | Block 1 | 2 | DMSO | 34.8 | 49.9 | 79.3 | 150 |
| 6 | F1 | Block 1 | 3 | DMSO | 21.24 | 37.32 | 69.48 | 185 |
| 7 | A2 | Block 1 | 0.5 | Water | 77.6 | 100 | 100 | 69 |
| 8 | B2 | Block 1 | 0.75 | Water | 67.5 | 88.3 | 100 | 87 |
| 9 | C2 | Block 1 | 1 | Water | 49.6 | 62.8 | 99.7 | 94.3 |
| 10 | D2 | Block 1 | 1.5 | Water | 36.6 | 49.5 | 76.3 | 107 |
| 11 | E2 | Block 1 | 2 | Water | 29.9 | 39.8 | 59.5 | 124.6 |
| 12 | F2 | Block 1 | 3 | Water | 19.46 | 35.98 | 69.2 | 139.3 |

The impact of water and DMSO in the occurrence of water on the prescription release from the polymer matrix, the polymer shows continuous release of the drug (sustained release) because in occurrence of water the polymer is hydrated, and the drug has to travel more distance to come out from the polymer matrix. From the FIG. 7A-D, it can be seen that the actual release value and the predicted release value are almost coming in the straight line concluding that the prepared formulation is significant.

Under the studied experimental domain, the ideal formulation was searched by numerical optimization technique. The limitation was set for the intended objectives and the whole experimental area was checked for compositions under which the set limits were satisfied to maximum. The limits set for numerical optimization, resulting optimized solution, formulations, related reaction values and desirability values are presented in Table 5.

TABLE 5

Constraints set for numeric optimization.

| Name | Goal | Lower Limit | Upper Limit | Lower Weight | Upper Weight | Importance |
|---|---|---|---|---|---|---|
| Polymer | is in range | 0.5 | 3 | 1 | 1 | 3 |
| Solvent | is in range | Water | DMSO | 1 | 1 | 3 |
| Rel 24 | is target = 36.1093 | 19.46 | 91 | 1 | 1 | 3 |
| Rel 48 | is target = 49.2496 | 35.98 | 100 | 1 | 1 | 3 |
| Rel 96 | is target = 76.1418 | 59.5 | 100 | 1 | 1 | 3 |
| Vis | is target = 84.6073 | 69 | 185 | 1 | 1 | 3 |

The effects achieved by numeric optimization are the three best options for the three categories which categories as polymer, water and DMSO. The solutions comply with the goal requirements of the full release and least viscosity at low to intermediate ratio of Polymer:Drug (0.5:1-3:1). In conclusion, solution 1 was chosen as an optimal formulation that was suitable in the range 0.83 and the response variables values were within the desired range. 1.55:1 contained GG:Drug ratio formulation and 47% minimum release water solvent at 24 h, 76% maximum release at 96 hours and 109 cP of minimum viscosity.

Figure 8:
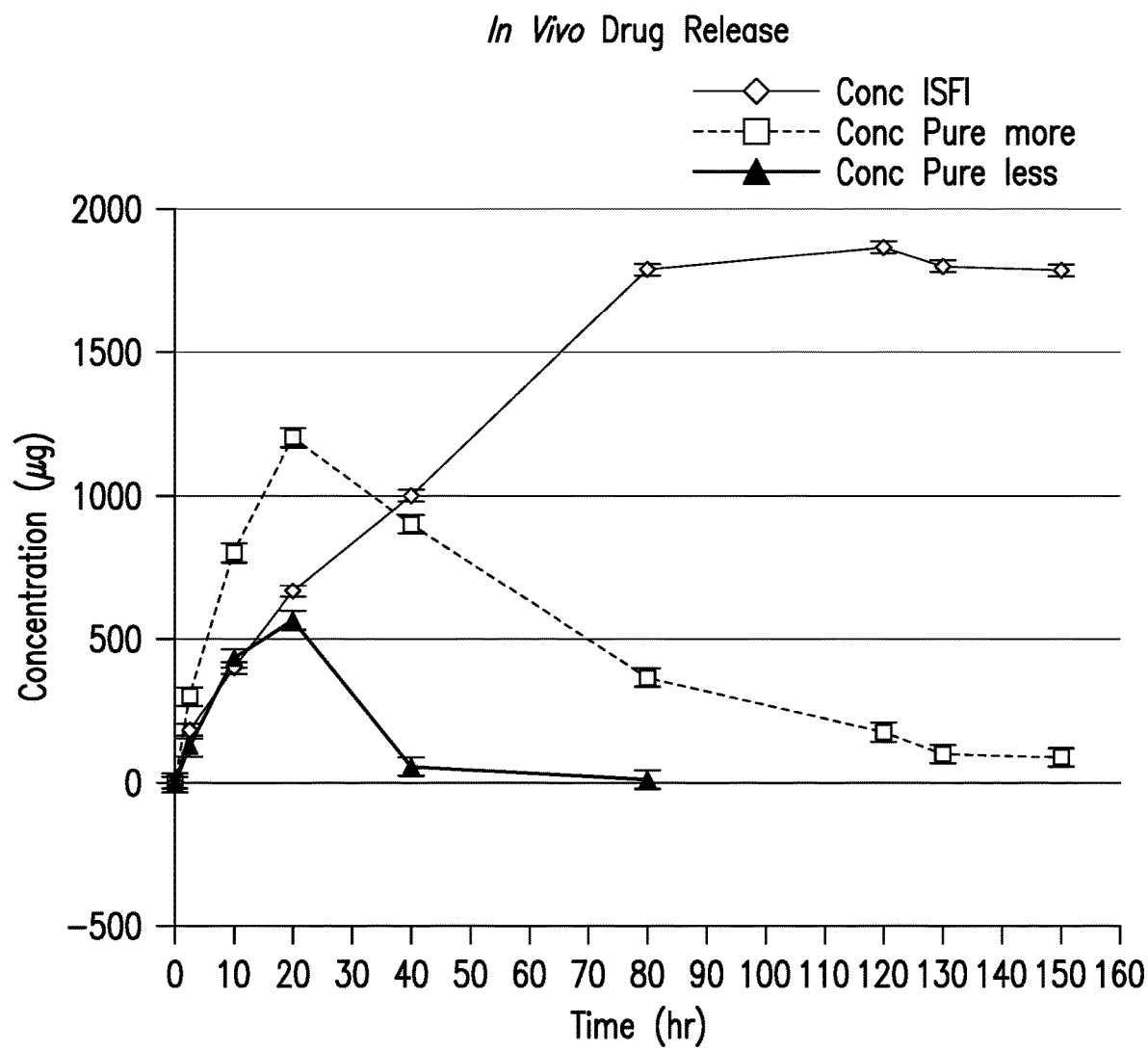
FIG. 8 shows in vivo drug release from the composition of the present disclosure.
Figure 9:
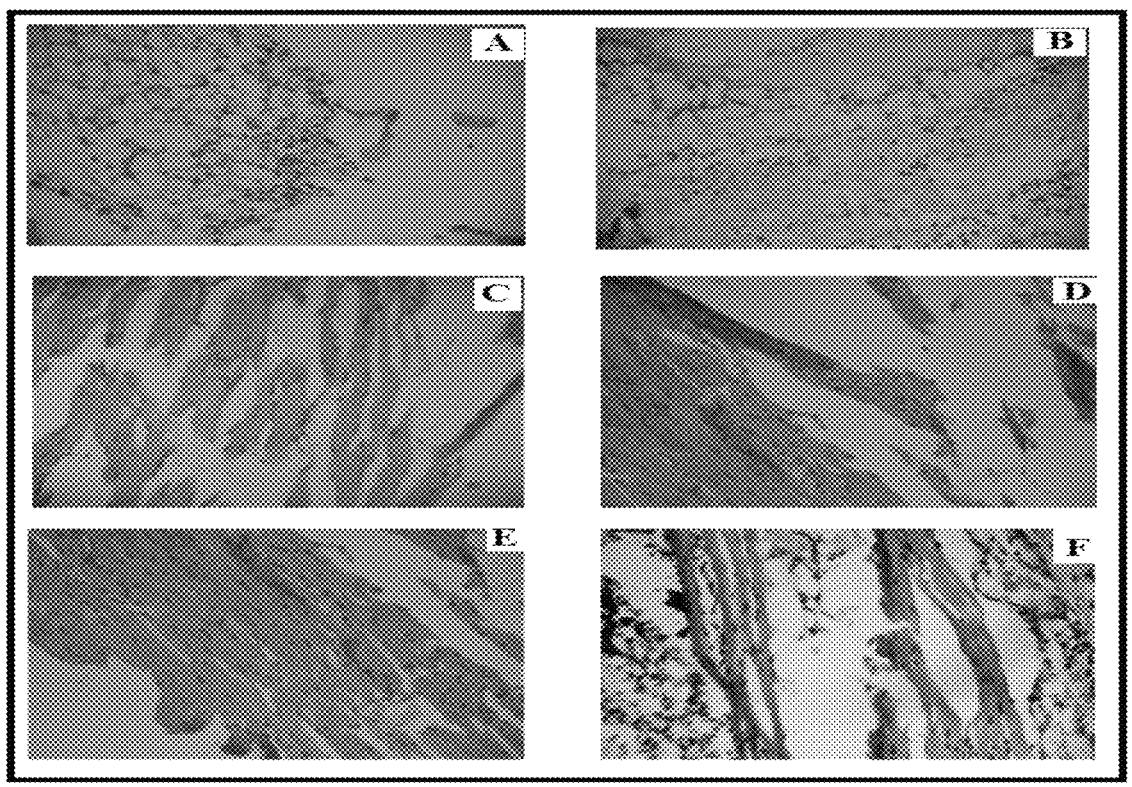
FIG. 9 shows images of (A) transverse section of normal subcutaneous tissue of rat, (B) transverse section of rat subcutaneous tissue on day 3 of blank ISFI administration, (C) transverse section of rat subcutaneous tissue on day 3 of pure DMF administration, (D) transverse section of rat subcutaneous tissue on day 3 of optimized ISFI administration, (E) transverse section of rat subcutaneous tissue on day 7 of optimized ISFI administration, and (F) transverse section of rat subcutaneous tissue on day 14 after the optimized ISFI administration.

All animals remained in good health throughout the acclimatization and study periods. The cumulative (±SD) plasma concentrations of DMF at the times of sample collection after SC are plotted in FIG. 8. Drug concentration was determined by using HPLC method. In individual animal the plasma concentration time profiles of DMF counting the values of the respective mean and standard deviation (±SD) and was given a respective treatment like group I given a pure drug (2 mg/0.2 mL), group II treated with the formulation of DMF ISFI D2 (2 mg/0.2 mL), and pure drug (1 mg/0.2 mL) as group III. S.C. route was chosen for all the prepared formation. By putting the first order kinetics into the plasma concentration of DMF data the pharmacokinetic data study and modeling were studied on rats. The lowest $C_{max}$ and $T_{max}$ was found to be in group III by in vivo pharmacokinetic analysis. The maximum $C_{max}$ 1864.8 µg/mL and $T_{max}$, 120 h were observed respectively in Group II. In Group I, the plasma concentration falls after 150 hours. The plasma concentration falls to non-detectable quantities in group III animals. As shown in FIG. 8, constant steady state plasma concentration were preserved by the ISFI formulation and even after 168 hours it remained within the effective levels. So, the effective and sustained control release of DMF were advised by pharmacokinetic analysis and the therapeutic concentration was maintained in the rat model for 168 hours. By combining the seven DMF conventional doses into optimized DMF ISFI single s.c. dose formulation (D2) the result was attained. Seven conventional, s.c., injections (168 h therapy) of DMF could be replaced by this delivery system. Since a substantial drug concentration has been identified on plasma samples up to 150 hours, it is possible to change the established ISFI system by dose adjustment and control of drug discharges in vitro to substitute or replace seven traditional doses (168 h therapy).

During the physical inspection, a significant inflammatory reaction was observed with redness in group I and group II rats but mild in placebo or ISFI without drug-treated animals of group III. Group I animals exhibited highest inflammation followed by group II and minimal inflammation was detected in group III. The findings show that, like most of the drugs are stuck mostly in implant with only a tiny amount of pure drug contacting the tissues at the implant site at any point of time, so the ISFI formulation has given certain protection from inflammatory reaction. These findings demonstrate the character of the DMF and support the data shown in FIG. 8.

It can be resolved by the result of the present experimental work that crosslinking the GG with L-Cysteine can improve the gelling properties i.e., reduction in gelation time, viscosity and reduced immunogenic properties associated with the unmodified GG, can be used in formulation ISFI. And the in situ forming implant can be a promising delivery vehicle for any potent drug having shorter half-life. It is an efficacious formulation with reduced side effects caused by frequent dosing of drug and thus can be helpful in the treatment many life-threating diseases like Multiple Sclerosis and myelodysplastic syndrome.

REFERENCES

Anderson, J. M., Langone, J. J., 1999. Issues and perspectives on the biocompatibility and immunotoxicity evaluation of implanted controlled release systems. J. Control Rel. 57, 107-113.

Babu, M., Yadav, K. S. Y., Moin, A., Shivakumar, H. G., 2011. In vitro-In vivo evaluation of poly(2-hydroxyethyl methacrylate-co-methyl methacrylate) hydrogel implants containing cisplatin. Acta Pharmaceutica Sinica B. 1(4), 261-267.

Chandrasekaran, R., Puigjaner, L. C., Joyce, K. L., Arnott, S., 1988. Cation interactions in gellan: An x-ray study of the potassium salt. Carbo. Res. 181, 23-40.

Crescenzi, V., Dentini, M., Coviello, T., Rizzo, R., 1986. Comparative analysis of the behavior of gellan gum (S-60) and welan gum (S-130) in dilute aqueous solution. Carbo. Res. 149 (2), 425-32.

Dai, L., Liu, X. X., Tong, Z., 2010. Critical behavior at sol-gel transition in Gellan gum aqueous solutions with KCl and CaCl2 of different concentrations. Carbohydrate Polymers. 81(2), 207-212.

Daniel, W., (1983). Multiple regression and correlation. In: Biostatistics: A foundation for analysis in the health sciences, third ed. John Wiley and Sons, New York, 317-351.

Deasy, P. B., Karen, J. Q., 1991. Rheological evaluation of deacetylated gellan gum (Gelrite) for pharmaceutical use. International Journal of Pharmaceutics. 13, 117-123.

Eliaz, R. E., Kost, J., 2000. Characterization of a polymeric PLGA-injectable implant delivery system for the controlled release of proteins. J. Biomed. Mat. Res. 50(3), 388-96.

Hatefi, A., Amsden, B., 2002. Biodegradable injectable in situ forming drug delivery systems. Journal of Controlled Release. 80, 9-28.

Krauland, A. H., Leitner, V. M., Bernkop-Schnürch., 2003. Improvement in the in situ gelling properties of deacetylated gellan gum by the immobilization of thiol groups. Journal of pharmaceutical sciences. 92(6), 1234-41.

Kapoor, D. N., Katare, O. P., Dhawan, S., 2012. In situ forming implant for controlled delivery of an anti-HIV fusion inhibitor. International Journal of Pharmaceutics. 426, 132-143.

Nakajima, K., Ikehara, T., Nishi, T., 1996. Observation of gellan gum by scanning tunneling microscopy. Carbo. Poly. 30(2-3), 77-81.

Ogawa, E., Takahashi, R., Yajima, H., Nishinari, K., 2006. Effects of molar mass on the coil to helix transition of sodium-type gellan gums in aqueous solutions. Food Hydrocoll 20(2-3), 378-85.

Packhaeuser, C. B., Schnieders, J., Oster, C. G., Kissel, T., 2004. In situ forming parenteral drug delivery systems: an overview. European Journal of Pharmaceutics and Biopharmaceutics. 58, 445-455.

Park, H., Park, K., 1999. Biocompatibility issues of implantable drug delivery systems. Pharm. Res. 13, 1770-1776.

Singh, B., Dahiya, M., Saharan, V., Ahuja, N., 2005. Optimizing drug delivery systems using systematic design of experiments. Part II. Retrospect and prospects. Crit. Rev. Ther. Drug Carrier Syst. 22, 215-293.

Singh, B., & Ahuja, N., 2004. Response surface optimization of drug delivery system. In: Jain, N. K. (Ed.), Progress in Controlled and Novel Drug Delivery Systems, $1^{st}$ ed. CBS Publishers, New Delhi.

Skjåk-Bræk, G., Grasdalen, H., Smidsrød, O., 1989. Inhomogeneous polysaccharide ionic gels, Carbo. Poly. 10(1), 31-54.

It is to be understood that this invention is not limited to any particular embodiment described herein and may vary. It is also to be understood that the terminology used herein is for the purpose of describing particular embodiments only, and is not intended to be limiting, since the scope of the present invention will be limited only by the appended claims.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to ante-date such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

What is claimed is:

1. An injectable drug delivery implant composition, comprising:
- a biodegradable water-soluble polymer, wherein the polymer is gellan gum crosslinked with L-cysteine, wherein the gellan gum crosslinked with L-cysteine is present at a concentration of 1-2% w/w based on the total weight of the composition;
- a biocompatible solvent; and
- a therapeutically effective amount of a biologically active agent, wherein the biologically active agent is dimethyl fumarate (DMF) or pharmaceutically acceptable salts thereof, wherein the gellan gum crosslinked with L-cysteine and the DMF or pharmaceutically acceptable salt thereof are at a weight ratio of about 0.5:1 to 3:1, and wherein the composition is in a liquid form and is configured to undergo gelation to form a gel-like implant in situ after injection into a subject.

2. The composition of claim 1, wherein the gellan gum crosslinked with L-cysteine is present at a concentration of 1.5% w/w based on the total weight of the composition.

3. The composition of claim 1, wherein the biocompatible solvent is water present at a concentration of 5-25% v/v of the composition.

4. The composition of claim 1, wherein the biocompatible solvent is DMSO present at a concentration of 5-25% v/v of the composition.

5. The composition of claim 1, wherein the gellan gum crosslinked with L-cysteine and the DMF or pharmaceutically acceptable salt thereof are at a weight ratio that allows release of 40-60% of DMF or pharmaceutically acceptable salt thereof after 24-48 hours of the injection.

6. A method of treating a subject suffering from multiple sclerosis (MS), comprising:
- parenterally injecting under the skin of the subject a composition comprising a biodegradable water-soluble polymer, wherein the polymer is gellan gum crosslinked with L-cysteine, wherein the gellan gum crosslinked with L-cysteine is present at a concentration of 1-2% w/w based on the total weight of the composition;
- a biocompatible solvent; and
- a therapeutically effective amount of a biologically active agent, wherein the biologically active agent is dimethyl fumarate (DMF) or pharmaceutically acceptable salts thereof, wherein the gellan gum crosslinked with L-cysteine and the DMF or pharmacologically acceptable salt thereof are at a weight ratio of about 0.5:1 to 3:1, wherein the biologically active agent is released from the gellan gum crosslinked with L-cysteine over time, pharmaceutically acceptable salt thereof and wherein the composition is parenterally injected once per week or less often.

7. The method of claim 6, wherein the gellan gum crosslinked with L-cysteine is present at a concentration of 1.5% w/w based on the total weight of the composition.

8. The method of claim 6, wherein the biocompatible solvent is water present at a concentration of 5-25% v/v of the composition.

9. The method of claim 6, wherein the biocompatible solvent is DMSO present at a concentration of 5-25% v/v of the composition.

10. The method of claim 6, wherein the gellan gum crosslinked with L-cysteine and the DMF or pharmaceutically acceptable salt thereof are at a weight ratio that allows release of 40-60% of DMF or pharmaceutically acceptable salt thereof after 24-48 hours of the injection.

* * * * *

UNITED STATES PATENT AND TRADEMARK OFFICE
CERTIFICATE OF CORRECTION

PATENT NO. : 11,590,071 B2  
APPLICATION NO. : 17/367967  
DATED : February 28, 2023  
INVENTOR(S) : Kazmi et al.

Page 1 of 1

It is certified that error appears in the above-identified patent and that said Letters Patent is hereby corrected as shown below:

On the Title Page

The inventors names and addresses should be corrected to read as follows:
Imran Kazmi, Jeddah (SA); Hemant Yadav, Ras Al Khaimah (UAE); Fahad A. Al-Abbasi, Jeddah (SA); Muhammad Shahid Nadeem, Jeddah (SA); Hisham N. Altayb, Jeddah (SA); Muhammad Afzal, Sakaka (SA); Gaurav Gupta, Jaipur (IN); Abhay Raizaday, Jaipur (IN)

Signed and Sealed this  
Fourth Day of April, 2023

Katherine Kelly Vidal  
*Director of the United States Patent and Trademark Office*